United States Patent
Hayashi et al.

(10) Patent No.: US 9,561,992 B2
(45) Date of Patent: Feb. 7, 2017

(54) ALKYLATED DIPHENYL ETHER COMPOUND AND LUBRICATING OIL CONTAINING SAID COMPOUND

(71) Applicant: MORESCO CORPORATION, Kobe-shi, Hyogo (JP)

(72) Inventors: Mayumi Hayashi, Kobe (JP); Shingo Maruyama, Kobe (JP)

(73) Assignee: MORESCO CORPORATION, Kobe-shi (JP)

( * ) Notice: Subject to any disclaimer, the term of this patent is extended or adjusted under 35 U.S.C. 154(b) by 0 days.

(21) Appl. No.: 14/395,880

(22) PCT Filed: Oct. 30, 2013

(86) PCT No.: PCT/JP2013/080059
§ 371 (c)(1),
(2) Date: Oct. 21, 2014

(87) PCT Pub. No.: WO2014/069670
PCT Pub. Date: May 8, 2014

(65) Prior Publication Data
US 2015/0225327 A1    Aug. 13, 2015

(30) Foreign Application Priority Data
Oct. 31, 2012  (JP) ................. 2012-240243

(51) Int. Cl.
*C10M 105/18* (2006.01)
*C07C 43/275* (2006.01)
*C07C 43/263* (2006.01)

(52) U.S. Cl.
CPC .......... *C07C 43/275* (2013.01); *C07C 43/263* (2013.01); *C10M 105/18* (2013.01); *C10M 2207/0406* (2013.01); *C10N 2230/08* (2013.01)

(58) Field of Classification Search
CPC ... C07C 43/275; C07C 43/263; C10M 105/18; C10M 2207/0406; C10N 2230/08
(Continued)

(56) References Cited

U.S. PATENT DOCUMENTS 3,999,960 A * 12/1976 Langer, Jr. ................. C10L 1/16
  44/440
4,014,663 A *  3/1977 Feldman .................. C10L 1/143
  210/749
(Continued)

FOREIGN PATENT DOCUMENTS

JP        58-22515 B2    5/1983
JP        2572814 B2     1/1997
(Continued)

OTHER PUBLICATIONS

International Search Report dated Feb. 10, 2014 issued in corresponding application No. PCT/JP2013/080059.
(Continued)

*Primary Examiner* — James Goloboy
(74) *Attorney, Agent, or Firm* — Westerman, Hattori, Daniels & Adrian, LLP

(57) ABSTRACT

A compound of the formula (2)

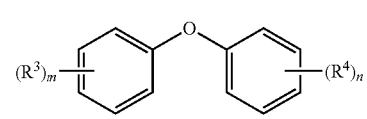

(2)

wherein $R^3$ and $R^4$ are the same or different and are a branched hydrocarbon group having 10 to 26 carbon atoms,
(Continued)

42 to 100 mole % of the benzylic carbons of each $R^3$ and $R^4$ are quaternary, m and n are each a real number of at least zero, and $2.0 \leq m+n \leq 3.0$.

19 Claims, 10 Drawing Sheets

(58) Field of Classification Search
 USPC .......................................... 508/581; 568/629
 See application file for complete search history.

(56) References Cited

U.S. PATENT DOCUMENTS

| | | | |
|---|---|---|---|
| 4,755,189 A | * | 7/1988 | Feldman ................. C10L 1/143 44/393 |
| 4,827,064 A | * | 5/1989 | Wu ........................ C10G 50/02 585/10 |
| 5,102,427 A | * | 4/1992 | Feldman ................. C10L 1/14 44/408 |
| 5,171,915 A | * | 12/1992 | Forbus ................. C10M 105/06 560/103 |
| 2008/0234157 A1 | | 9/2008 | Yoon et al. |

FOREIGN PATENT DOCUMENTS

| | | |
|---|---|---|
| JP | 2000-345178 A | 12/2000 |
| JP | 2007-332240 A | 12/2007 |
| JP | 2008-208174 A | 9/2008 |
| JP | 2010-522258 A | 7/2010 |
| JP | 2012-102051 A | 5/2012 |

OTHER PUBLICATIONS

Kono, "Practical examples and effects of phenyl ether-based synthetic lubricants", Lubrication Economy, Dec. 5, 2000, vol. 417, pp. 18-23.

Nozaki et al., "Technical trend of bearing for electric auxiliary machine", NTN Technical Review, No. 65, 1996, pp. 65-72; with partial translation.

* cited by examiner

ALKYLATED DIPHENYL ETHER COMPOUND AND LUBRICATING OIL CONTAINING SAID COMPOUND

TECHNICAL FIELD

The present invention relates to a diphenyl ether compound substituted with hydrocarbon group and a lubricant containing the compound for high temperature use.

BACKGROUND ART

In recent years, lubricants such as lubricating oil or lubricating grease are used under a severe condition such as high temperature, high speed and high load with downsizing and lightweighting of various machines and bearings, high speed processing and maintenance-free systems. Therefore, lubricants are become indispensable which have superior heat resistance and oxidation resistance.

In bearing lubrication, under high temperature and high-speed condition, a lubricating oil or grease used for lubrication causes a temperature increase due to oil film shortage or heat and oxidative degradation. As a result, a base oil of lubricant is promoted to evaporate to form sludge, damage the bearing and decrease a life of machine.

Therefore, various lubricating oils and greases are investigated which are usable at high temperature condition. Generally, an improvement of the lubricants under a high temperature condition highly depends on a base oil of lubricant which is contained at largest amount. Examples of such heat-resistant base oils are polyphenyl ether, silicone oil and fluorinate oil (for example, non-patent literature 2). However, polyphenyl ether and fluorinated oil are generally very expensive, and silicone oil is said to be generally disadvantageous in lubricity.

It is important to take a balance between cost and performance of the base oil for providing lubricating oils and greases which are low-cost but high-performance. Lubricating oil for high temperatures and heat-resistant grease are known which use alkyl diphenyl ether as a base oil (e.g., HILUBE LB-100, MORESCO Corporation) (for example, patent literatures 1 and 2, non-patent literature 1). Alkyl diphenyl ether is excellent in stability to heat and oxidation, causes particularly a little evaporation in use under high temperature, and small in viscosity variation. Further, when heat-resistant grease containing alkyl diphenyl ether as a base oil is used for a ball bearing and a roller bearing, it is apparent that brittle separation by hydrogen brittleness of metal materials extremely decreases which is caused by invasion of hydrogen to the steel which occurs in fixed rings (for example, non-patent literature 2). Because such a characteristic is hardly available by other general-purpose synthetic lubricants, e.g., α-olefin oligomer, polyalkylene glycols, ester-based oil, a heat-resistant grease lubricating oil which is relatively inexpensive and superior property can be obtained using alkyl diphenyl ether.

With the above superior property, a heat-resistant grease using the alkyl diphenyl ether as a base oil and urea or lithium hydroxystearate as a thickener can be used in a wide temperature range from low to high temperatures, and is widely used for a bearing for automobile electric auxiliary machine such as an alternator which requires long life and long-term reliability.

However, in recent years, these automobile electric auxiliary parts become inferior in thermal dissipation due to downsizing and lightweighting of the parts. Therefore, the heat-resistant grease for bearing is used under more severe condition than usual in view of temperature environment, and more improvement of the base oil is expected.

At present, alkyl diphenyl ether is prepared by an addition reaction of diphenyl ether and a linear α-olefin such as 1-dodecene or 1-tetradecene, and a ratio of the carbon at benzyl position being quaternary is 30 to 40 mole %. This alkyl diphenyl ether is expected to be more improved in heat-resistance.

PRIOR ART LITERATURE

Patent Literature 1: JP 1983-22515B
Patent Literature 2: JP Patent No. 2572814
Non-patent Literature 1: Masatsugu Kono, Practical examples and effects of phenyl ether-based synthetic lubricants, Lubrication Economy, Dec. 5, 2000, Vol. 417 (December 2000), p 18-23
Non-patent Literature 2: Seiichi Nozaki et al, Technical trend of bearing for electric auxiliary machine, NTN TECHNICAL REVIEW, No. 65 (1996), p 65-72

SUMMARY OF THE INVENTION

Problem to be Solved by the Invention

An object of the present invention is to provide an alkyl diphenyl ether which maintains flowability at low temperature of the conventional alkyl diphenyl ether and superior heat stability (particularly less susceptible to be oxidized by heat) when used as a base oil for various lubricants such as lubricating oil or grease.

Means for Solving the Problem

The present invention provides the following compound and lubricant.
1. A compound of the formula (2)

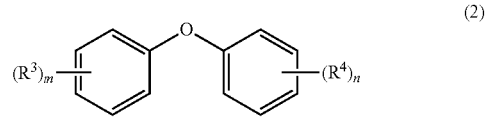

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

2. A compound of the formula (2) obtained by an addition reaction of diphenyl ether and a branched α-olefin of the formula (1) or its corresponding branched alkyl halide

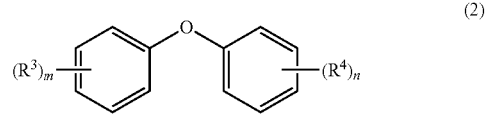

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

3. A compound of the formula (2) obtained by an addition reaction of diphenyl ether derivative of the formula (3) and a branched α-olefin of the formula (1) or its corresponding branched alkyl halide

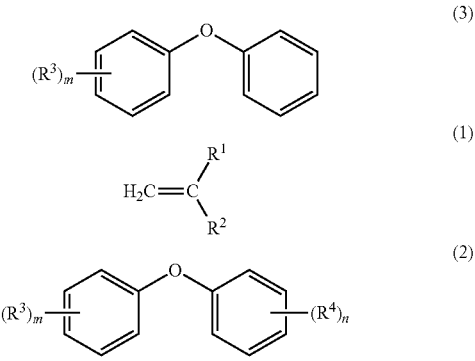

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

4. A compound of the formula (2) as defined in any one of the above items 1 to 3 wherein a ratio of the carbon at benzyl position being quaternary is 45 to 95 mole %.

5. A compound of the formula (2) as defined in any one of the above items 1 to 3 wherein 50 to 90 mole % of the benzylic carbons of each $R^3$ and $R^4$ are quaternary.

6. A compound of the formula (2) as defined in any one of the above items 1 to 3 wherein 50 to 65 mole % of the benzylic carbons of each $R^3$ and $R^4$ are quaternary.

7. A compound of the formula (2) as defined in any one of the above items 1 to 5 wherein $R^3$ and $R^4$ are each 1-butyl-1-methylheptyl, 1-methyl-1-pentyloctyl, 1-hexyl-1-methylnonyl, 1-heptyl-1-methyldecyl, 1-methyl-1-octylundecyl or 1-decyl-1-methyltridecyl.

8. A lubricating oil which is usable at high temperature containing a compound of the formula (2)

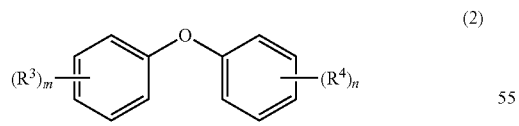

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

Effects of the Invention

The compound of the present invention, though having a larger molecular weight, exhibits equal flowability at low temperature to the conventional, well known and practically used alkyl diphenyl ether, small evaporation loss at high temperature and excellent stability to oxidation. Therefore, the present compound is usable as a base oil for lubricants such as lubricating oil or heat-resistant grease usable at further high temperature.

EMBODIMENT OF PRACTICING THE INVENTION

The present invention provides a compound of the formula (2)

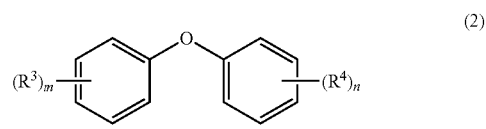

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

The compound of the formula (2) of the present invention is obtained by an addition reaction of diphenyl ether and a branched α-olefin of the formula (1) or its corresponding branched alkyl halide

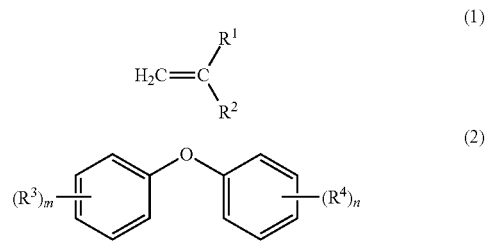

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$.

The compound of the formula (2) of the present invention is also obtained by an addition reaction of diphenyl ether derivative of the formula (3) and a branched α-olefin of the formula (1) or its corresponding branched alkyl halide

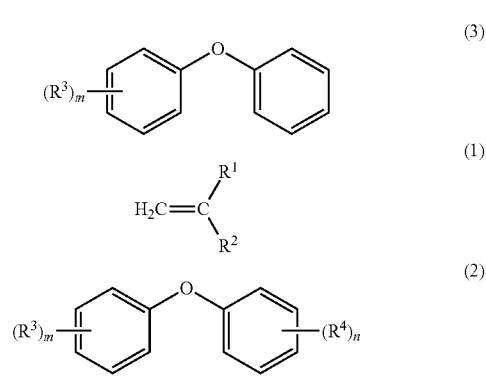

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and 2.0≤m+n≤3.0.

Diphenyl ether is represented by $C_6H_5OC_6H_5$.

In the compound of the formula (1), $R^1$ and $R^2$ are the same or different and are a hydrocarbon group having 4 to 12 carbon atoms. Examples thereof are butyl, hexyl, octyl, decyl and dodecyl. $R^1$ and $R^2$ are preferably hydrocarbon group having 6 to 10 carbon atoms.

A compound of the formula (1a) can be used as a compound of the formula (1)

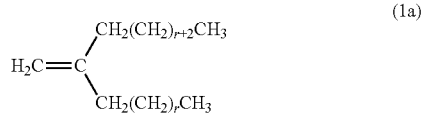

wherein r is an integer of 2 to 10, preferably 4 to 8.

Examples of compound of the formula (1) are 2-butylhexene, 2-butyloctene, 2-pentylnonene, 2-hexyloctene, 2-hexyldecene, 2-octyldecene, 2-octyldodecene, 2-decyldodecene, 2-decyltetradecene and 2-dodecylhexadecene.

Examples of compound of the formula (1a) are 2-butyloctene, 2-pentylnonene, 2-hexyldecene, 2-heptylundecene, 2-octyldodecene and 2-decyltetradecene.

In the compound of the formula (2), $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and 2.0≤m+n≤3.0.

Examples of $R^3$ and $R^4$ are the following branched hydrocarbon group.

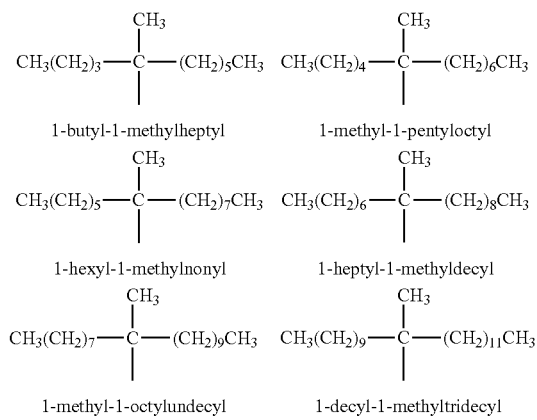

In the compound of the formula (2) of the present invention, when $R^3$ and $R^4$ are less than 10 in carbon number, excess amount of evaporation occurs, and when more than 26 in carbon number, viscosity and pour point are too high. These hydrocarbon groups may bond to any position of any of two aromatic rings of diphenyl ether. $R^3$ and $R^4$ are preferably hydrocarbon groups having 16 to 20 carbon atoms.

The compound of the formula (2) of the present invention can be prepared by, for example, Friedel-Crafts reaction of diphenyl ether or diphenyl ether derivative of the formula (3) with branched α-olefin or its corresponding branched alkyl halide using aluminum chloride as a catalyst. Alkyl diphenyl ether wherein di- or more alkylated diphenyl ether is contained as a main component can also be obtained by removing low-boiling compounds such as an unreacted starting compound or monoalkylated diphenyl ether having one alkyl group by distillation or the like.

In the following, the present process is explained in more detail with showing an example.

A catalyst is added to diphenyl ether or diphenyl ether derivative of the formula (3) and the mixture is heated at usually 100 to 130° C. to dissolve the catalyst homogeneously in diphenyl ether or diphenyl ether derivative of the formula (3). Then, a branched α-olefin or its corresponding branched alkyl halide is added dropwise in an amount of 1 to 2 equivalents to one equivalent of diphenyl ether or diphenyl ether derivative of the formula (3) while maintaining 110 to 125° C. for usually 2.5 to 4.5 hours. After completing the dropwise addition, the reaction is conducted at 110 to 125° C. for 5 to 40 minutes. By adding dropwise, it is possible to prevent α-olefin or its corresponding branched alkyl halide from polymerization such as dimerization. The reaction mixture is allowed to cool to 90° C., then alkali neutralizing agent is added and stirred at 80 to 90° C. for 30 minutes. Then, activated clay is added and the mixture is heated with stirring at 80 to 90° C. for 0.5 to 3 hours. The mixture is allowed to cool to 30° C., then filtered at reduced pressure and distilled at reduced pressure to obtain the desired product.

Examples of branched α-olefins are 2-butyloctene, 2-hexyldecene and 2-octyldodecene.

Examples of branched alkyl halide are 2-butyloctyl chloride, 2-hexyldecyl chloride and 2-octyldodecyl chloride.

Generally, in case of reacting a diphenyl ether derivative of the formula (3) and a branched α-olefin of the formula (1), theoretically it is considered that to benzene ring bonds hydrocarbon group wherein all of the benzylic carbons are quaternary. However, it is assumed that various reactions occur due to inner isomerization of olefin, and peaks of hydrogen which bond to the benzylic carbons (secondary carbon or tertiary carbon) are found to exist by NMR analysis. These peaks will not exist when all of the benzylic carbons are quaternary. Therefore, in the present invention, addition number of quaternary hydrocarbon group (X) is obtained from the following Analytical Example 1 and this value is defined as ratio of the benzylic carbons being quaternary.

Analytical Example 1

Calculation of Alkyl Addition Number, and Addition Number of Branched Hydrocarbon Group Wherein the Benzylic Carbon is Quaternary From $^1$H-NMR spectrum of a model compound such as FIG. 19, alkyl addition number, and addition number of branched hydrocarbon group wherein the benzylic carbon is quaternary are calculated.

a (chemical shift 6.5~7.3) shows peak of hydrogen in benzene ring.

b1 (chemical shift 2.8~3.3) and b2 (chemical shift 2.2~2.7) show peak of hydrogen in benzylic position.

c (chemical shift 0.5~1.9) shows peak of hydrogen in alkyl group.

Based on integrated values (ratio) of peaks of a, b1, b2 and c, the addition numbers are calculated by the following equations.

Alkyl addition number $(m+n)=10(b1+b2+c)/[(\text{average hydrogen number of alkyl group})a+b1+b2+c]$ In case of $m=1$, Alkyl addition number $(m+n)=1+[\{9(b1+b2+c)-(\text{average hydrogen number of alkyl group } m)a\}/\{(\text{average hydrogen number of alkyl group } n)a+b1+b2+c\}]$ Addition number of quaternary hydrocarbon group $(X)=(m+n)-[\{b1+(b2+2)\}\times\{10-(m+n)\}]$ In the compound of the formula (2) of the present invention, m and n are each a real number of at least zero, and $2.0 \leq m+n \leq 3.0$. When less than 2.0, excess amount of evaporation occurs, and when more than 3.0, viscosity and pour point are too high. The compound of the formula (2) may contain monoalkylated diphenyl ether in an amount of about 0.1 to 20 mole %.

In the compound of the formula (2) of the present invention, $R^3$ and $R^4$ are each a branched hydrocarbon group having 10 to 26 carbon atoms, and 42 to 100 mole %, preferably 45 to 95 mole %, more preferably 50 to 90 mole %, particularly preferably 50 to 65 mole % of the benzylic carbons of each $R^3$ and $R^4$ are quaternary.

The present invention provides a lubricating oil which is usable at high temperature containing a compound of the formula (2)

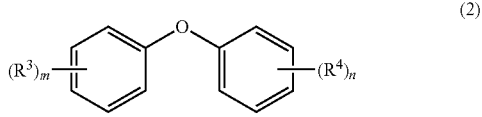

(2)

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$. The compound of the formula (2) is not limited to one obtained by the present process but those obtained by any process are usable.

To the present lubricating oil can be added, other than the compound of the formula (2), mineral oil, synthetic oils such as α-olefin oligomer, polyol ester, diester, polyalkylene glycol, silicone oil and modified silicone oil. Further, as required, an additive can be added to the present lubricating oil such as anti-wear agent, extreme pressure agent, antioxidant, viscosity index improver, pour point depressant and, rust and corrosion inhibitor. In the present lubricating oil, it is preferable to contain 10 to 99% by weight of the compound of the formula (2), 0 to 90% by weight of mineral oil or synthetic oil, and 1 to 10% by weight of the additive. The present lubricating oil for high temperature can be used as bearing oil, fluid bearing oil, oil-impregnated bearing oil, grease base oil, oil-impregnated plastics oil, gear oil, jet engine oil, adiabatic engine oil, gas turbine oil, automatic transmission fluid, vacuum pump oil and hydraulic fluid which are usable at high temperature.

EXAMPLES

The invention will be described in more detail with reference to the following examples and comparative examples to which, however, the invention is not limited. An alkali neutralizing agent used below is Kyoward 1000 [$Mg_{4.5} \cdot Al_2(OH)_{13} \cdot CO_3 \cdot 3.5H_2O$] of Kyowa Chemical Industry Co., Ltd.

Example 1

Preparation of Compound 1

Figure 1:
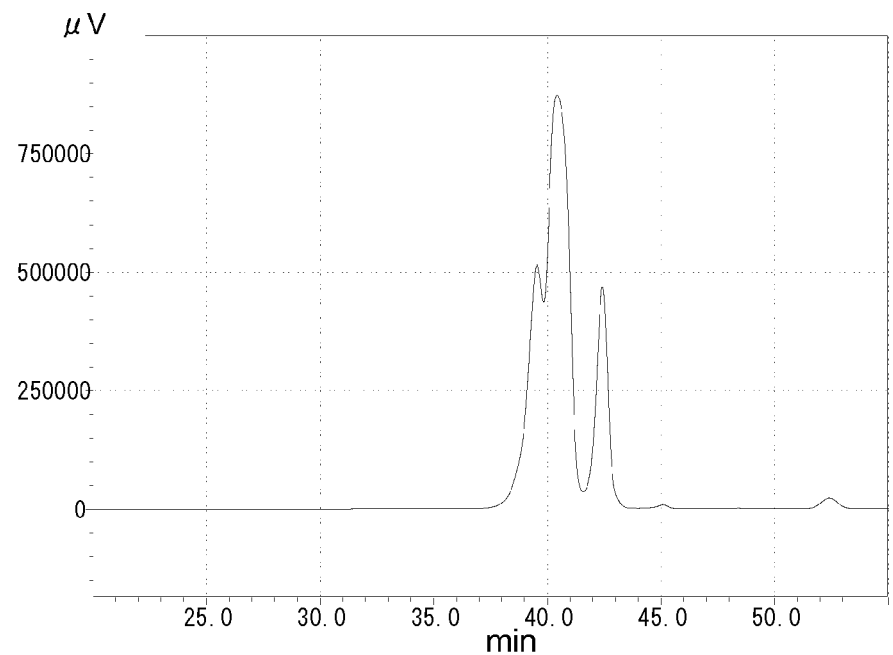
FIG. 1 is GPC spectrum of Compound 1.
Figure 2:
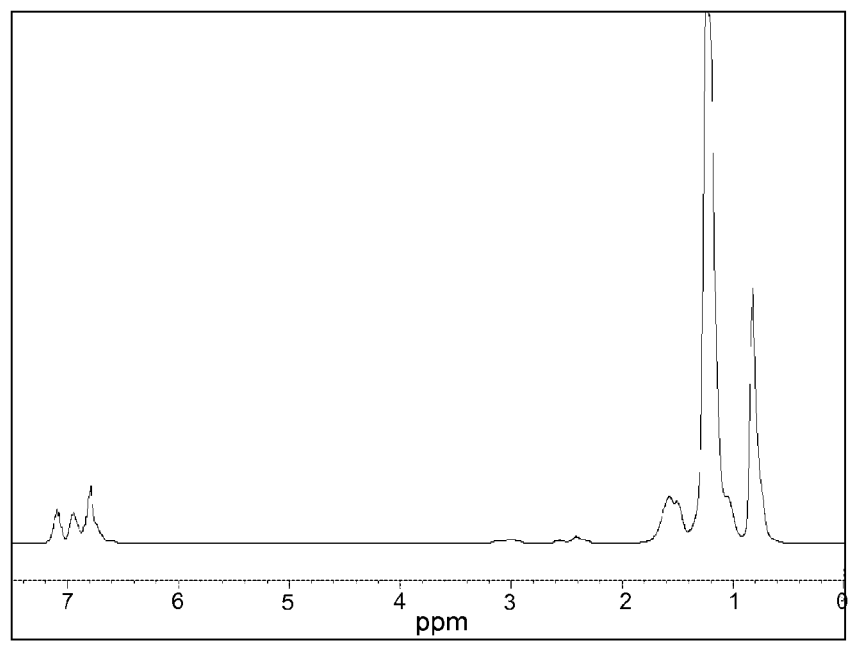
FIG. 2 is $^1$H-NMR spectrum of Compound 1.

To a four-necked flask having 10 liter volume equipped with a stirrer, dropping funnel, thermometer and condenser were placed 2800 g (16.5 moles) of diphenyl ether and 32 g (0.24 mole) of anhydrous aluminum chloride. After dissolving anhydrous aluminum chloride with heating at 110° C., to the mixture was added dropwise 4600 g (16.5 moles) of 2-octyldodecene while maintaining the temperature at 110° C. for 4.5 hours to perform an addition reaction. After completion of dropwise addition, the mixture was stirred at 110° C. for 30 minutes, then allowed to cool to 90° C., and thereto added 300 g of alkali neutralizing agent and stirred for 30 minutes. To the mixture was added 150 g of activated clay, stirred at 90° C. for one hour and removed aluminum chloride and other acid substances by-produced by filtration at reduced pressure. Then, removing unreacted starting material and monoalkylated diphenyl ether by distillation at reduced pressure of 2.5 to 3.5 torr at 250 to 324° C., thereby 3210 g of alkyl diphenyl ether wherein dialkylated diphenyl ether was contained as a main component was obtained. The product also contained a part of monoalkylated diphenyl ether. The product (referred to as Compound 1) contained 18.2 mole % of monoalkylated diphenyl ether and alkyl addition number was 2.00 from GPC spectrum (FIG. 1) and 1H-NMR spectrum (FIG. 2). The ratio of the benzylic carbons being quaternary was 58.0 mole %.

GPC
Retention time of monoalkylated diphenyl ether: 41.789~43.886 18.2 mole %
Retention time of dialkylated diphenyl ether: 40.083~41.789 56.6 mole %
Retention time of trialkylated diphenyl ether: 37.595~40.083 25.2 mole %
$^1$H-NMR (solvent: none, standard substance: none)
Integrated value of δ=6.5~7.3 ppm is 1,
integrated value of δ=2.8~3.3 ppm is 0.06,
integrated value of δ=2.2~2.7 ppm is 0.09,
integrated value of δ=0.5~1.9 ppm is 10.10.

GPC system of Shimadzu Corp. was used. The system was as follows. CBM-20A (system controller), DGU-20A3 (online degasser for three channels), LC-20AD (liquid feed unit for high-precision analysis), SIL-20A (auto-sampler), RID-10A (refractive index detector) and SPD-20A (UV-VIS detector).

In the measurement, three KF-803L columns, THF (mobile phase) and SPD-20A (detector) were used. Flow rate was 30 MPa.

$^1$H-NMR was measured by using a nuclear magnetic resonance device, JNM-ECX400 of JEOL Ltd. at 80° C. without solvent and standard substance.

Chemical shift was obtained by conducting the measurement using the same compound, deuterated chloroform as solvent and TMS as standard substance. This is why peaks of deuterated chloroform overlap with those of benzene ring and precious integrated values are unavailable.

The ratio of each alkyl-adducted compound such as monoalkyl-adducted compound was calculated from each peak area of GPC spectrum. In case a peak is not an independent peak, the ratio was calculated from each peak area obtained by drawing a perpendicular line from valley of neighboring two peaks.

Example 2

Preparation of Compound 2

Figure 3:
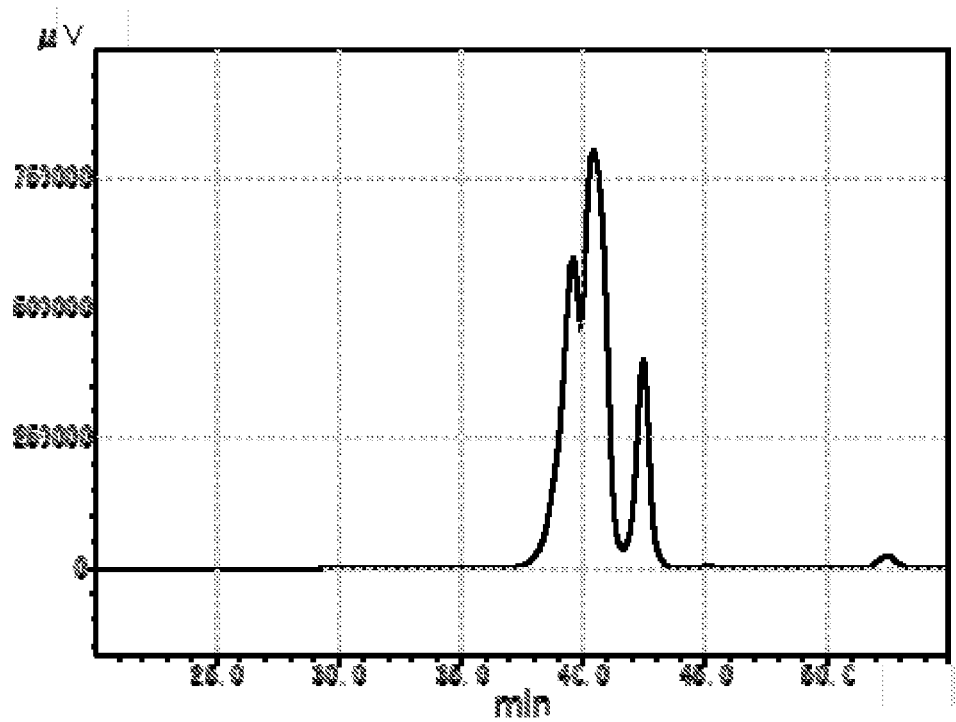
FIG. 3 is GPC spectrum of Compound 2.
Figure 4:
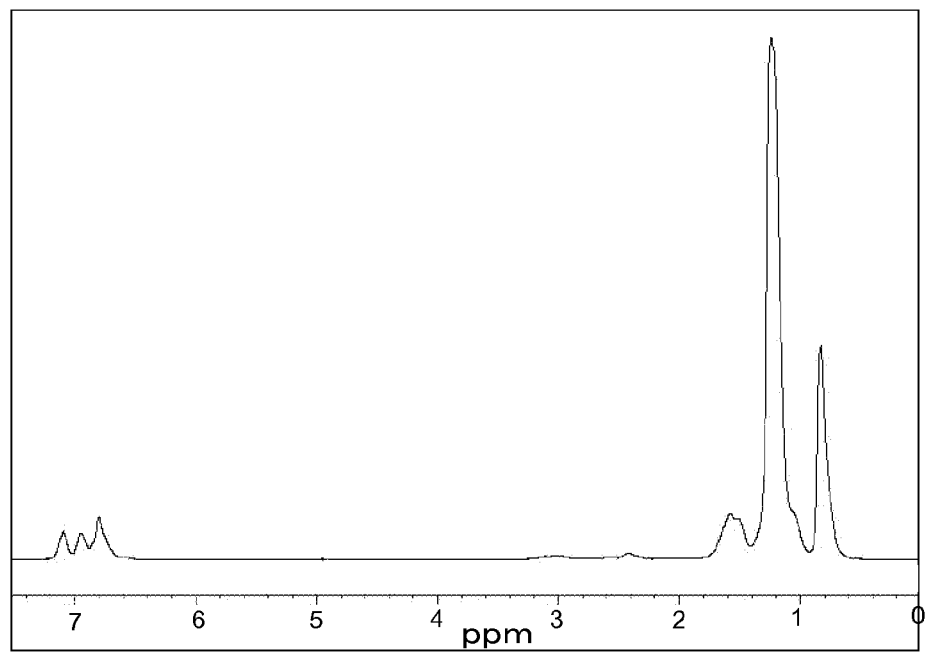
FIG. 4 is $^1$H-NMR spectrum of Compound 2.

The experiment was conducted in the same manner as in Example 1 except that 1900 g (11.2 moles) of diphenyl ether, 33 g (0.25 mole) of anhydrous aluminum chloride, 4700 g (16.8 moles) of 2-octyldodecene, 320 g of alkali neutralizing agent and 160 g of activated clay were used in a four-necked flask having 10 liter volume to obtain 3640 g of alkyl diphenyl ether wherein dialkylated diphenyl ether was contained as a main component. The product (referred to as Compound 2) contained 15.9 mole % of monoalkylated diphenyl ether and alkyl addition number was 2.13 from GPC spectrum (FIG. 3) and $^1$H-NMR spectrum (FIG. 4). The ratio of the benzylic carbons being quaternary was 57.5 mole %.

GPC
Retention time of monoalkylated diphenyl ether: 41.704~43.643 15.9 mole %
Retention time of dialkylated diphenyl ether: 40.028~41.704 50.5 mole %
Retention time of trialkylated diphenyl ether: 37.043~40.028 33.6 mole %
$^1$H-NMR (solvent: none, standard substance: none)
Integrated value of δ=6.5~7.3 ppm is 1,
integrated value of δ=2.8~3.3 ppm is 0.07,
integrated value of δ=2.2~2.7 ppm is 0.09,
integrated value of δ=0.5~1.9 ppm is 10.93.

Example 3

Preparation of Compound 3

Figure 5:
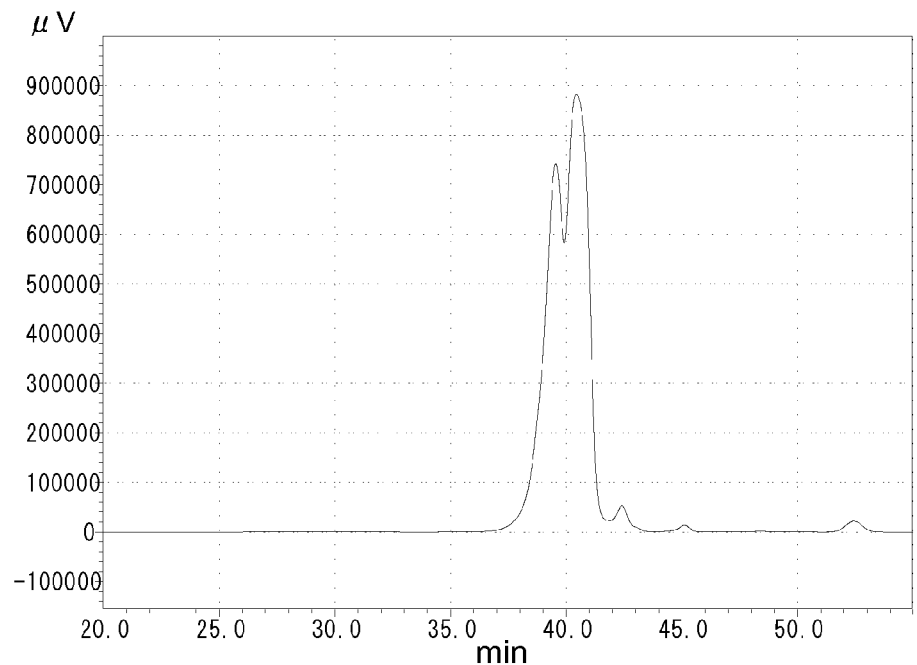
FIG. 5 is GPC spectrum of Compound 3.
Figure 6:
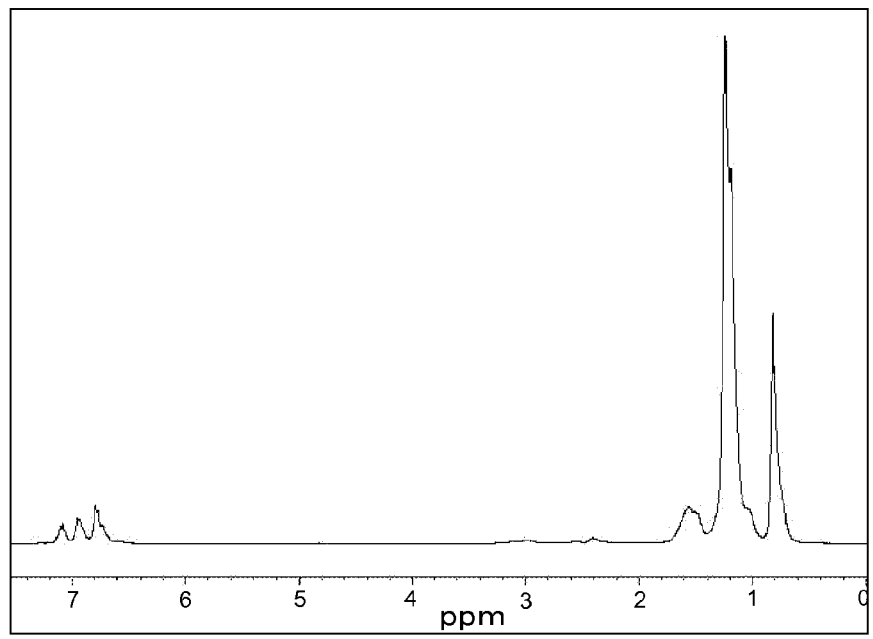
FIG. 6 is $^1$H-NMR spectrum of Compound 3.

To a four-necked flask having 2 liter volume equipped with a stirrer, dropping funnel, thermometer and condenser were placed 385 g (2.3 moles) of diphenyl ether and 6.7 g (0.05 mole) of anhydrous aluminum chloride. After dissolving anhydrous aluminum chloride with heating at 110° C., to the mixture was added dropwise 950 g (3.4 moles) of 2-octyldodecene while maintaining the temperature at 110° C. for 4.5 hours to perform an addition reaction. After completion of dropwise addition, the mixture was stirred at 110° C. for 30 minutes, then allowed to cool to 90° C., and thereto added 67 g of alkali neutralizing agent and stirred for 30 minutes. To the mixture was added 35 g of activated clay, stirred at 90° C. for one hour and removed aluminum chloride and other acid substances by-produced by filtration at reduced pressure. Then, removing unreacted starting material and monoalkylated diphenyl ether by distillation at reduced pressure of 0.1 to 0.5 torr at 250 to 324° C., thereby 800 g of alkyl diphenyl ether wherein dialkylated diphenyl ether was contained as a main component was obtained. The product (referred to as Compound 3) contained 2.1 mole % of monoalkylated diphenyl ether and alkyl addition number was 2.35 from GPC spectrum (FIG. 5) and $^1$H-NMR spectrum (FIG. 6). The ratio of the benzylic carbons being quaternary was 52.9 mole %.

GPC
Retention time of monoalkylated diphenyl ether: 42.048~43.696 2.1 mole %
Retention time of dialkylated diphenyl ether: 40.126~42.048 54.9 mole %
Retention time of trialkylated diphenyl ether: 37.562~40.126 43.0 mole %
$^1$H-NMR (solvent: none, standard substance: none)
Integrated value of δ=6.5~7.3 ppm is 1,
integrated value of δ=2.8~3.3 ppm is 0.09,
integrated value of δ=2.2~2.7 ppm is 0.11,
integrated value of δ=0.5~1.9 ppm is 12.42.

Example 4

Preparation of Compound 4

Figure 7:
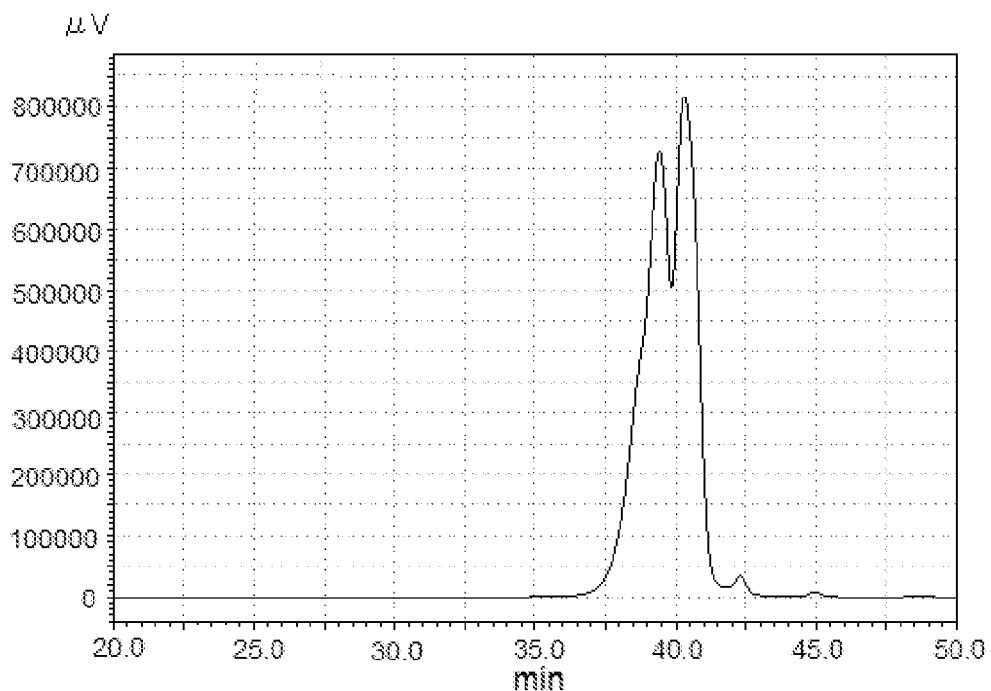
FIG. 7 is GPC spectrum of Compound 4.
Figure 8:
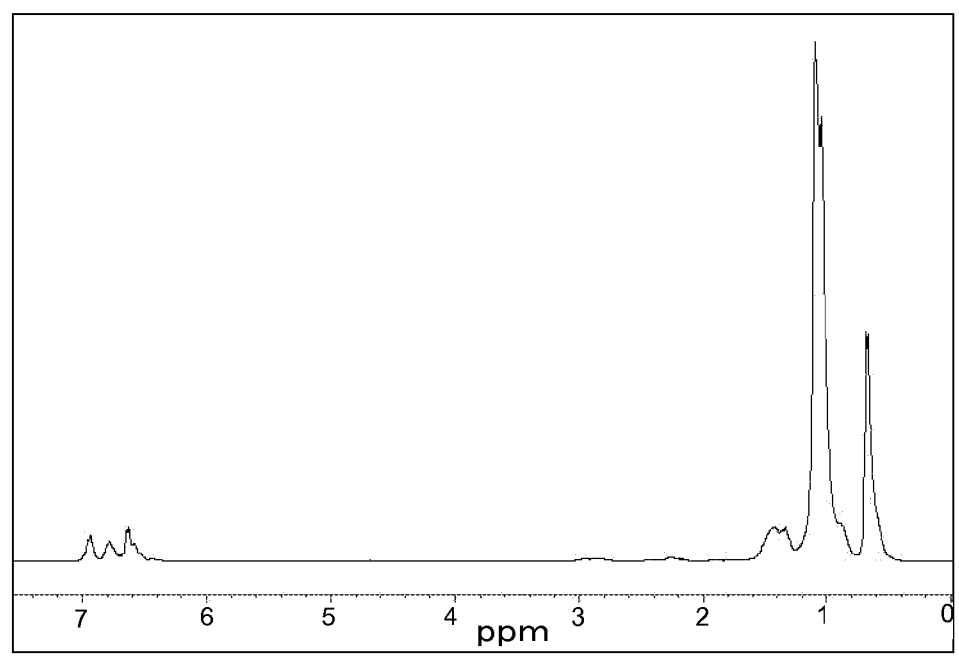
FIG. 8 is $^1$H-NMR spectrum of Compound 4.

The experiment was conducted in the same manner as in Example 3 except that 180 g (1.06 moles) of diphenyl ether, 4.2 g (0.032 mole) of anhydrous aluminum chloride, 594 g (2.12 moles) of 2-octyldodecene, 40 g of alkali neutralizing agent and 20 g of activated clay were used in a four-necked flask having 1 liter volume to obtain 490 g of alkyl diphenyl ether wherein dialkylated diphenyl ether was contained as a main component. The product (referred to as Compound 4) contained 1.3 mole % of monoalkylated diphenyl ether and alkyl addition number was 2.54 from GPC spectrum (FIG. 7) and $^1$H-NMR spectrum (FIG. 8). The ratio of the benzylic carbons being quaternary was 57.4 mole %.

GPC
Retention time of monoalkylated diphenyl ether: 41.761~43.395 1.3 mole %
Retention time of dialkylated diphenyl ether: 39.855~41.761 46.5 mole %
Retention time of trialkylated diphenyl ether: 35.907~39.855 52.2 mole %
$^1$H-NMR (solvent: none, standard substance: none)
Integrated value of δ=6.5~7.3 ppm is 1,
integrated value of δ=2.8~3.3 ppm is 0.09,
integrated value of δ=2.2~2.7 ppm is 0.11,
integrated value of δ=0.5~1.9 ppm is 13.74.

Example 5

Preparation of Compound 5

Figure 9:
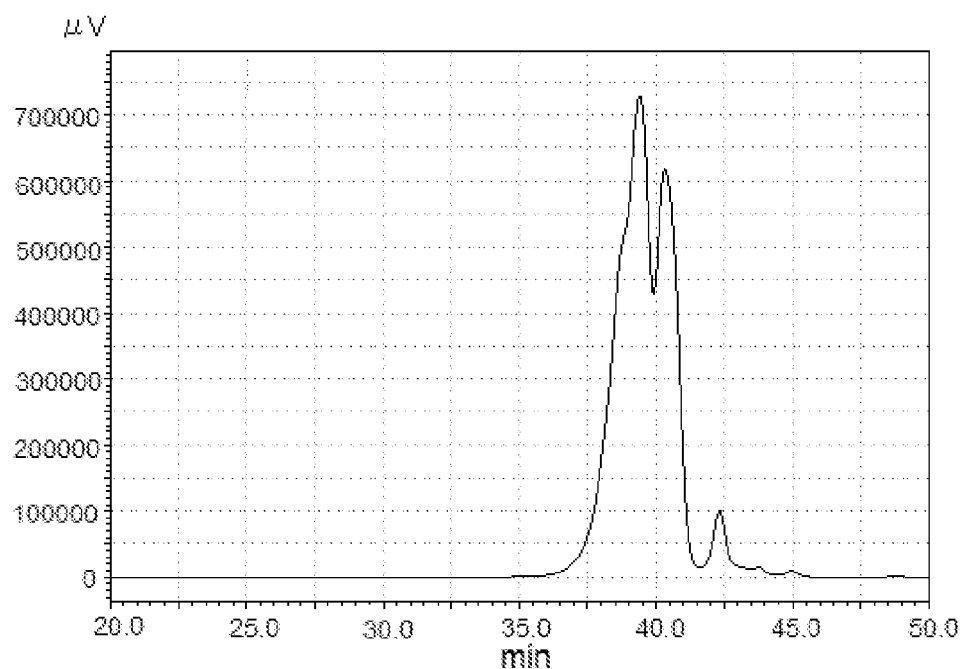
FIG. 9 is GPC spectrum of Compound 5.
Figure 10:
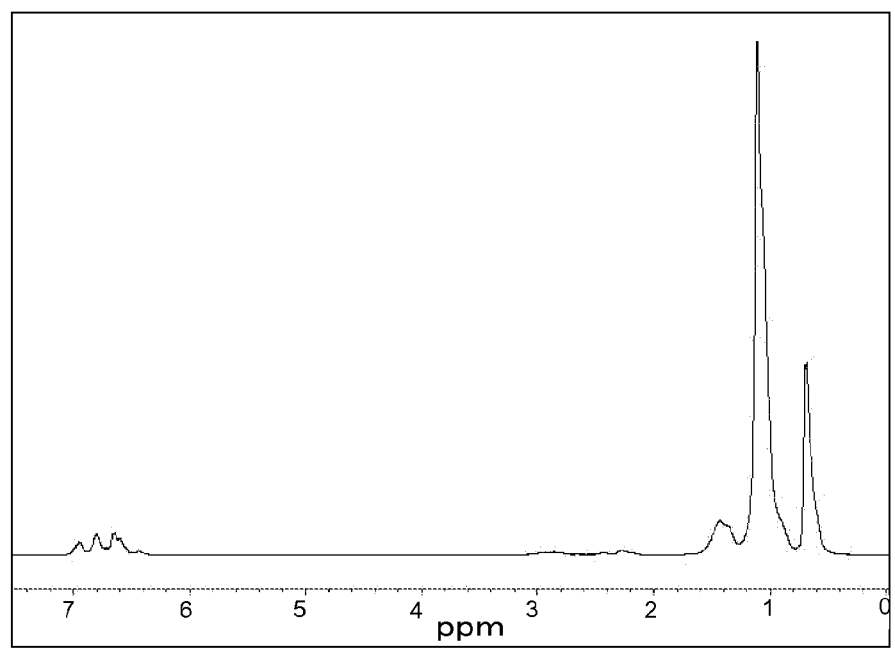
FIG. 10 is $^1$H-NMR spectrum of Compound 5.

The experiment was conducted in the same manner as in Example 3 except that 140 g (0.82 mole) of diphenyl ether, 4.8 g (0.036 mole) of anhydrous aluminum chloride, 690 g (2.46 moles) of 2-octyldodecene, 50 g of alkali neutralizing agent and 25 g of activated clay were used in a four-necked flask having 1 liter volume to obtain 630 g of alkyl diphenyl ether wherein dialkylated diphenyl ether was contained as a main component. The product (referred to as Compound 5) contained 3.9 mole % of monoalkylated diphenyl ether and alkyl addition number was 2.94 from GPC spectrum (FIG. 9) and 1H-NMR spectrum (FIG. 10). The ratio of the benzylic carbons being quaternary was 54.4 mole %.
GPC
Retention time of monoalkylated diphenyl ether: 41.726~43.545 3.9 mole %
Retention time of dialkylated diphenyl ether: 39.855~41.726 12.6 mole %
Retention time of trialkylated diphenyl ether: 35.514~39.855 83.5 mole %
$^1$H-NMR (solvent: none, standard substance: none)
Integrated value of $\delta$=6.5~7.3 ppm is 1,
integrated value of $\delta$=2.8~3.3 ppm is 0.12,
integrated value of $\delta$=2.2~2.7 ppm is 0.14,
integrated value of $\delta$=0.5~1.9 ppm is 16.84.

Example 6

Preparation of Compound 6

Figure 11:
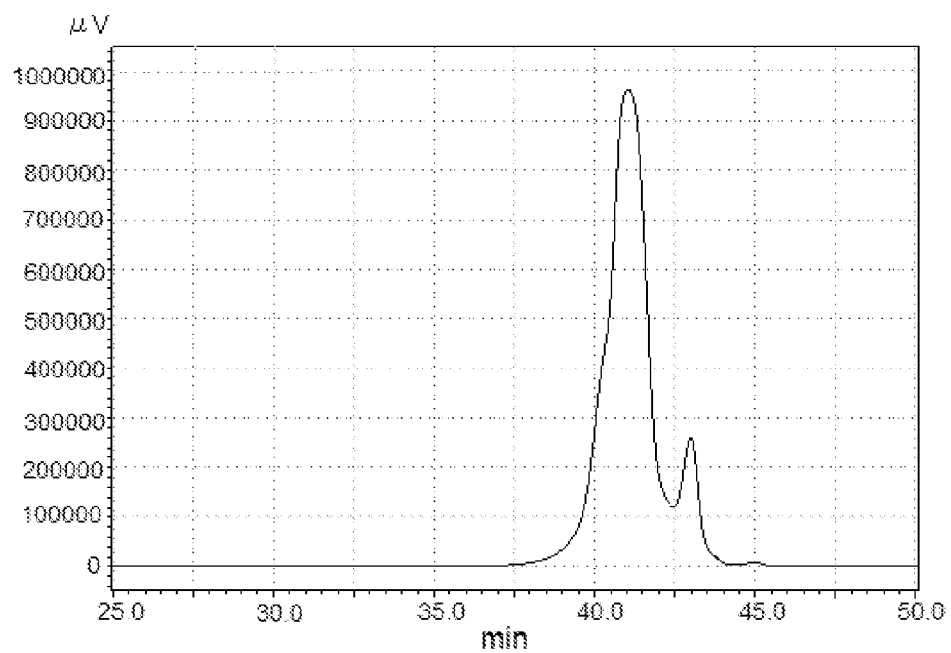
FIG. 11 is GPC spectrum of Compound 6.
Figure 12:
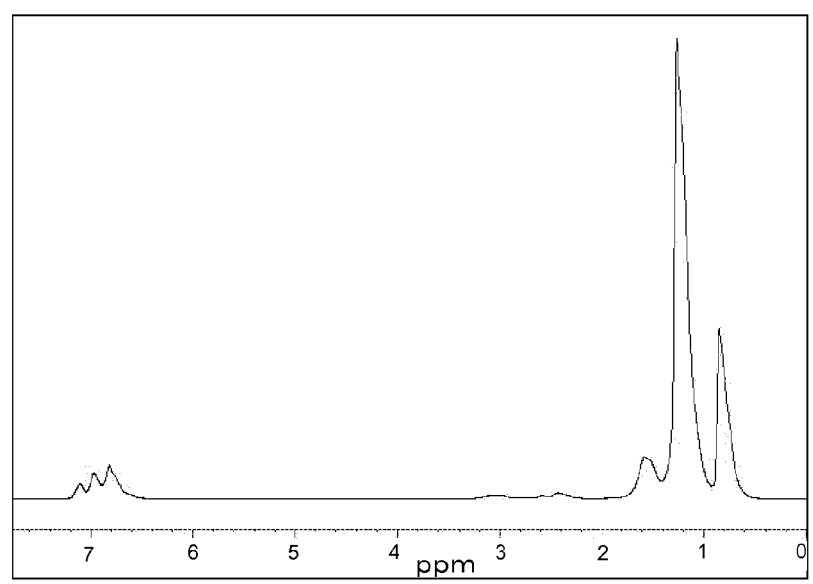
FIG. 12 is $^1$H-NMR spectrum of Compound 6.

The experiment was conducted in the same manner as in Example 1 except that 160 g (0.94 mole) of diphenyl ether, 3.1 g (0.023 mole) of anhydrous aluminum chloride, 316 g (1.41 moles) of 2-hexyldecene, 30 g of alkali neutralizing agent and 15 g of activated clay were used in a four-necked flask having 1 liter volume to obtain 240 g of alkyl diphenyl ether wherein dialkylated diphenyl ether was contained as a main component. The product (referred to as Compound 6) contained 10.9 mole % of monoalkylated diphenyl ether and alkyl addition number was 2.23 from GPC spectrum (FIG. 11) and $^1$H-NMR spectrum (FIG. 12). The ratio of the benzylic carbons being quaternary was 56.4 mole %.
GPC
Retention time of monoalkylated diphenyl ether: 42.467~44.297 10.9 mole %
Retention time of dialkylated diphenyl ether: 40.356~42.467 73.2 mole %
Retention time of trialkylated diphenyl ether: 36.369~40.356 15.9 mole %
$^1$H-NMR (solvent: none, standard substance: none)
Integrated value of $\delta$=6.5~7.3 ppm is 1,
integrated value of $\delta$=2.8~3.3 ppm is 0.08,
integrated value of $\delta$=2.2~2.7 ppm is 0.09,
integrated value of $\delta$=0.5~1.9 ppm is 9.20.

Comparative Example 1

Preparation of Compound 7

Figure 13:
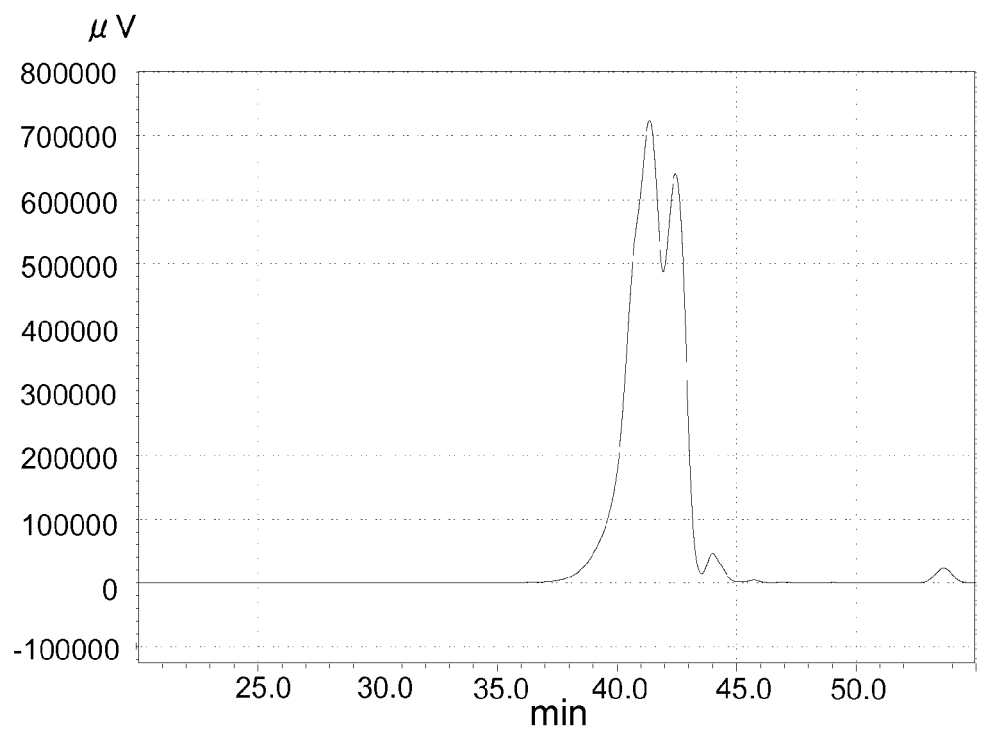
FIG. 13 is GPC spectrum of Compound 7.
Figure 14:
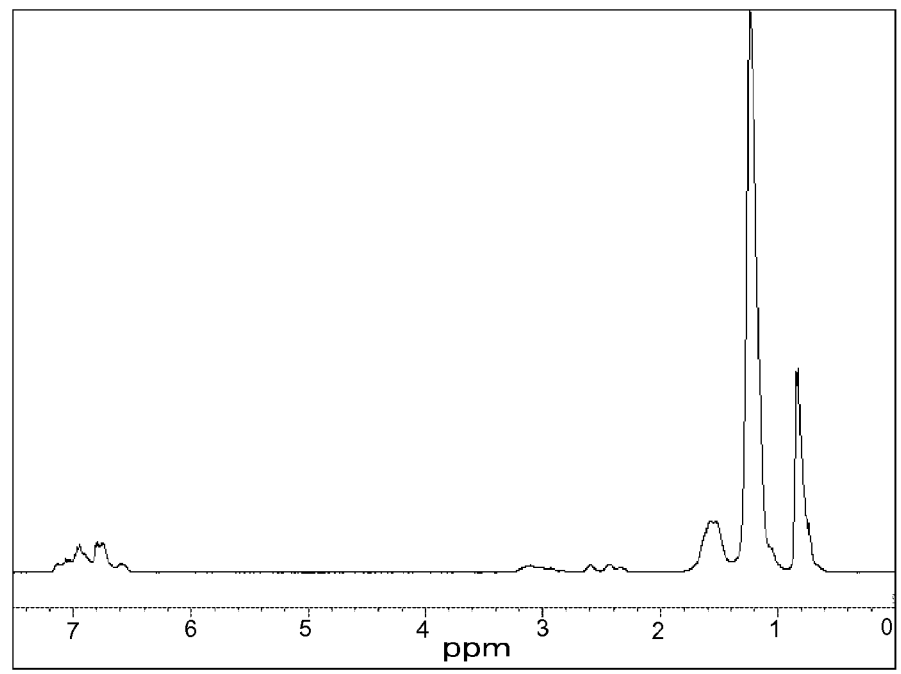
FIG. 14 is $^1$H-NMR spectrum of Compound 7.

To the same flask used in Example 1 were placed 1600 g (9.4 moles) of diphenyl ether and 15 g (0.11 mole) of anhydrous aluminum chloride. After dissolving anhydrous aluminum chloride with heating at 110° C., to the mixture was added dropwise a mixture of 1810 g (10.8 moles) of 1-dodecene and 1810 g (9.23 moles) of 1-tetradecene under nitrogen stream while maintaining the temperature at 110° C. for 4.5 hours to perform an addition reaction. After completion of dropwise addition, the mixture was stirred at 110° C. for 30 minutes, then allowed to cool to 90° C., and thereto added 68 g of alkali neutralizing agent and stirred for 30 minutes. To the mixture was added 68 g of activated clay, stirred at 90° C. for one hour and removed aluminum chloride and other acid substances by-produced by filtration at reduced pressure. Then, removing unreacted starting material and monoalkylated diphenyl ether by distillation at reduced pressure of 3.0 to 4.0 torr at 250 to 320° C., thereby 6000 g of alkyl diphenyl ether wherein dialkylated diphenyl ether was contained as a main component was obtained. The product (referred to as Compound 7) contained 1.8 mole % of monoalkylated diphenyl ether and alkyl addition number was 2.82 from GPC spectrum (FIG. 13) and $^1$H-NMR spectrum (FIG. 14). The ratio of the benzylic carbons being quaternary was 37.8 mole %.
GPC
Retention time of monoalkylated diphenyl ether: 43.766~45.224 1.8 mole %
Retention time of dialkylated diphenyl ether: 42.157~43.766 34.2 mole %
Retention time of trialkylated diphenyl ether: 37.328~42.157 64.0 mole %
Integrated value of $\delta$=6.5~7.3 ppm is 1,
integrated value of $\delta$=2.8~3.3 ppm is 0.16,
integrated value of $\delta$=2.2~2.7 ppm is 0.17,
integrated value of $\delta$=0.5~1.9 ppm is 10.30.

Comparative Example 2

Preparation of Compound 8

Figure 15:
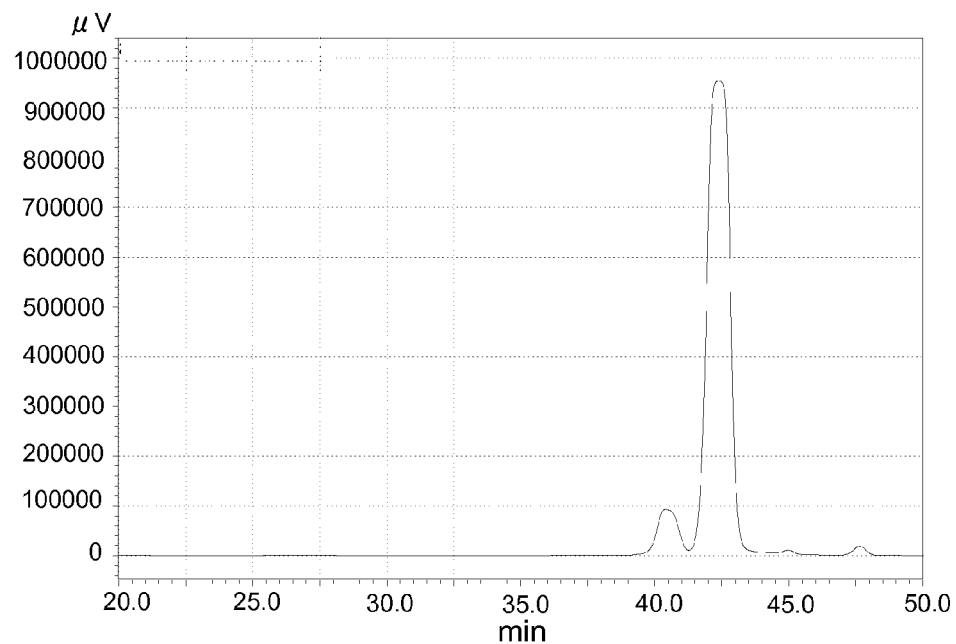
FIG. 15 is GPC spectrum of Compound 8.
Figure 16:
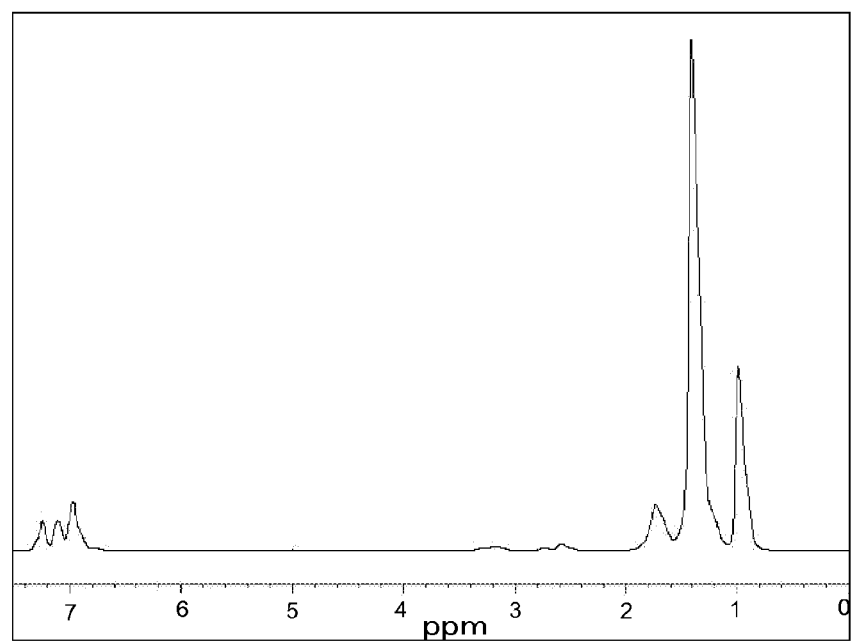
FIG. 16 is $^1$H-NMR spectrum of Compound 8.

To a four-necked flask having 2 liter volume equipped with a stirrer, dropping funnel, thermometer and condenser were placed 650 g (3.8 moles) of diphenyl ether and 4.6 g (0.035 mole) of anhydrous aluminum chloride. After dissolving anhydrous aluminum chloride with heating at 110° C., to the mixture was added dropwise 650 g (2.3 moles) of 2-octyldodecene while maintaining the temperature at 110° C. for 4.5 hours to perform an addition reaction. After completion of dropwise addition, the mixture was stirred at 110° C. for 30 minutes, then allowed to cool to 90° C., and thereto added 46 g of alkali neutralizing agent and stirred for 30 minutes. To the mixture was added 23 g of activated clay, stirred at 90° C. for one hour and removed aluminum chloride and other acid substances by-produced by filtration at reduced pressure. Then, removing monoalkylated diphenyl ether by distillation at reduced pressure of 2.5 to 3.5 torr at 280 to 315° C., thereby 940 g of alkyl diphenyl ether wherein dialkylated diphenyl ether was contained as a main component was obtained. The product (referred to as Compound 8) contained 91.8 mole % of monoalkylated diphenyl ether and alkyl addition number was 1.01 from GPC spectrum (FIG. 15) and $^1$H-NMR spectrum (FIG. 16). The ratio of the benzylic carbons being quaternary was 64.6 mole %.
GPC
Retention time of monoalkylated diphenyl ether: 41.272~44.395 91.8 mole %
Retention time of dialkylated diphenyl ether: 39.033~41.272 8.2 mole %
$^1$H-NMR (solvent: none, standard substance: none)
Integrated value of $\delta$=6.5~7.3 ppm is 1,
integrated value of $\delta$=2.8~3.3 ppm is 0.02,
integrated value of $\delta$=2.2~2.7 ppm is 0.04,
integrated value of $\delta$=0.5~1.9 ppm is 4.57.

Comparative Example 3

Preparation of Compound 9

Figure 17:
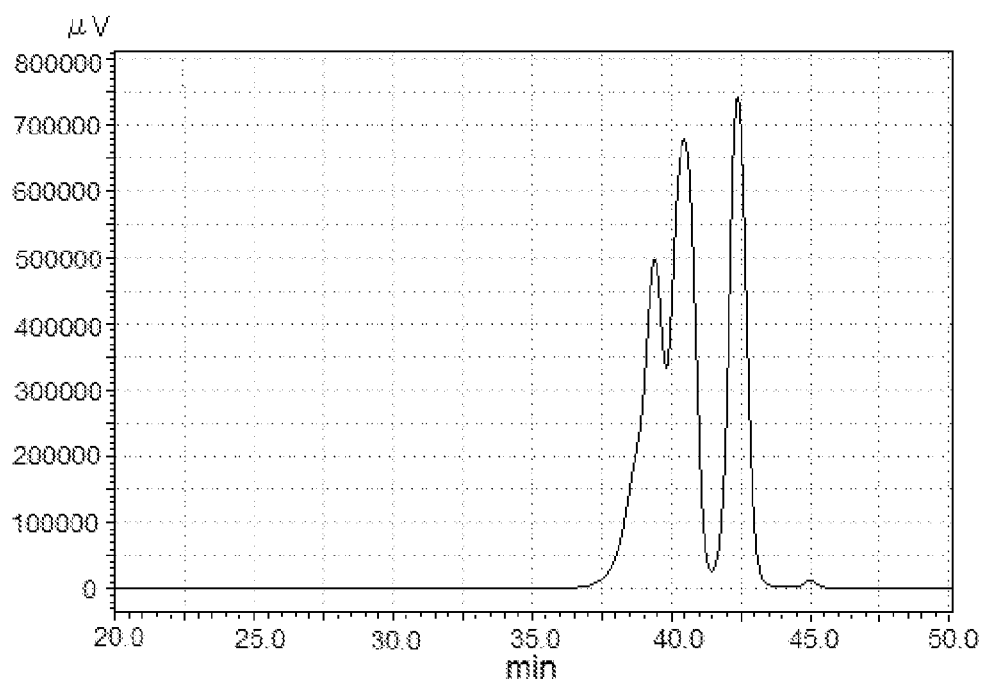
FIG. 17 is GPC spectrum of Compound 9.
Figure 18:
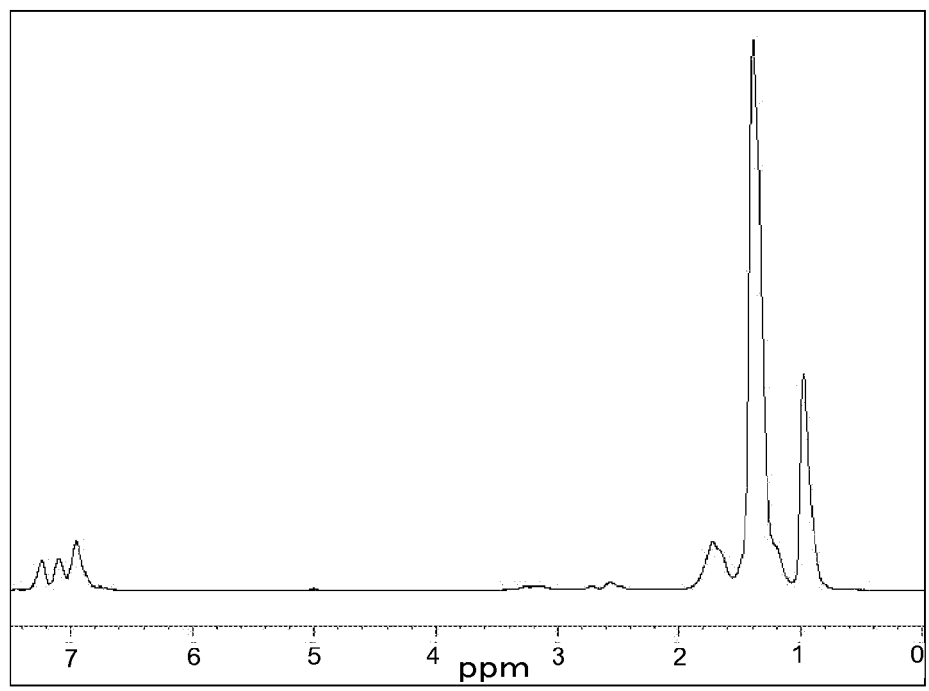
FIG. 18 is $^1$H-NMR spectrum of Compound 9.
Figure 19:
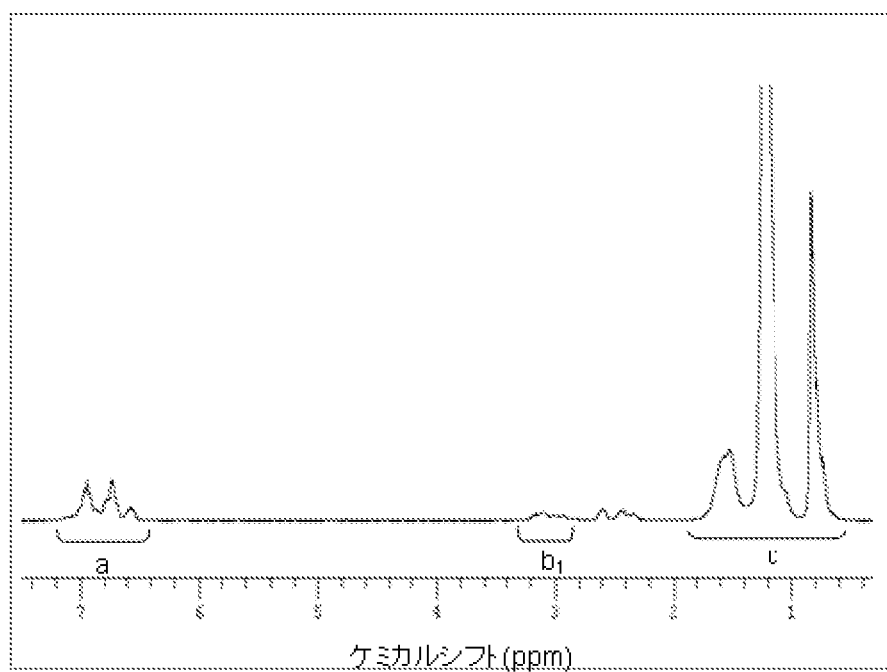
FIG. 19 is $^1$H-NMR spectrum of a model compound.

To a four-necked flask having 2 liter volume equipped with a stirrer, dropping funnel, thermometer and condenser were placed 415 g (2.4 moles) of diphenyl ether and 7.2 g (0.054 mole) of anhydrous aluminum chloride. After dissolving anhydrous aluminum chloride with heating at 110° C., to the mixture was added dropwise 1020 g (3.6 moles) of 2-octyldodecene while maintaining the temperature at 110° C. for 4.5 hours to perform an addition reaction. After completion of dropwise addition, the mixture was stirred at 110° C. for 30 minutes, then allowed to cool to 90° C., and thereto added 70 g of alkali neutralizing agent and stirred for 30 minutes. To the mixture was added 35 g of activated clay, stirred at 90° C. for one hour and removed aluminum chloride and other acid substances by-produced by filtration at reduced pressure. Then, removing unreacted starting material by distillation at reduced pressure of 2.5 to 3.5 torr at 250 to 285° C., thereby 1000 g of alkyl diphenyl ether wherein monoalkylated diphenyl ether and dialkylated diphenyl ether were contained as main components was obtained. The product (referred to as Compound 9) contained 32.3 mole % of monoalkylated diphenyl ether and alkyl addition number was 1.77 from GPC spectrum (FIG. 17) and $^1$H-NMR spectrum (FIG. 18). The ratio of the benzylic carbons being quaternary was 53.6 mole %.

GPC

Retention time of monoalkylated diphenyl ether: 41.468~44.081 32.3 mole %

Retention time of dialkylated diphenyl ether: 39.829~41.468 37.9 mole %

Retention time of trialkylated diphenyl ether: 35.665~39.829 29.8 mole %

$^1$H-NMR (solvent: none, standard substance: none)

Integrated value of δ=6.5~7.3 ppm is 1, integrated value of δ=2.8~3.3 ppm is 0.06, integrated value of δ=2.2~2.7 ppm is 0.08, integrated value of δ=0.5~1.9 ppm is 8.69.

Test Example 1

Heat Stability Test

In 30-ml glass beaker was weighed 20 g of each Compounds 1 to 9. Each sample was allowed to place in a thermostatic oven of 200° C. After 10 days or 20 days, the sample was checked for weight, kinematic viscosity and acid value. Change of properties by heat stability test was evaluated based on the values measured before the test.

Test Example 2

Fluidity at Low Temperature Test

Compounds 1 to 9 were checked for pour point according to JIS K2269.

Test Example 3

Lubricity Test

Friction coefficient was measured under a load of 0.98N and while raising the sample temperature from 25° C. to 250° C. by Ball on Plate friction tester using SUJ2 steel as Ball and SK-5 steel as Plate.

Table 1 shows the general properties, Table 2 the results of heat stability test, and Table 3 the results of lubricity test of Compounds 1 to 9.

TABLE 1

|  | Compound 1 Example 1 | Compound 2 Example 2 | Compound 3 Example 3 | Compound 4 Example 4 | Compound 5 Example 5 |
|---|---|---|---|---|---|
| alkyl group carbon number | branched-20 | branched-20 | branched-20 | branched-20 | branched-20 |
| monoalkyl adduct (mole %) | 18.2 | 15.9 | 2.1 | 1.3 | 3.9 |
| alkyl addition mole number | 2.00 | 2.13 | 2.35 | 2.54 | 2.94 |
| Properties |  |  |  |  |  |
| 40° C. kinematic viscosity (mm$^2$/s) | 141.2 | 151.4 | 180.4 | 217.8 | 277.4 |
| 100° C. kinematic viscosity (mm$^2$/s) | 15.40 | 16.34 | 18.63 | 21.53 | 26.35 |
| viscosity index | 122 | 114 | 116 | 118 | 124 |
| pour point (° C.) | −42.5 | −42.5 | −40.0 | −42.5 | −40.0 |

|  | Compound 6 Example 6 | Compound 7 Com. Ex. 1 | Compound 8 Com. Ex. 2 | Compound 9 Com. Ex. 3 |
|---|---|---|---|---|
| alkyl group carbon number | branched-16 | 12, 14 | branched-20 | branched-20 |
| monoalkyl adduct (mole %) | 10.9 | 1.8 | 91.8 | 32.3 |
| alkyl addition mole number | 2.23 | 2.82 | 1.01 | 1.77 |
| Properties |  |  |  |  |
| 40° C. kinematic viscosity (mm$^2$/s) | 142.3 | 102.6 | 39.0 | 103.5 |
| 100° C. kinematic viscosity (mm$^2$/s) | 15.82 | 12.60 | 5.921 | 12.46 |
| viscosity index | 116 | 116 | 92 | 113 |
| pour point (° C.) | −45.0 | −45.0 | −50 | −45 |

Table 1 confirms Compounds 1 to 6 which are branched alkylated diphenyl ether of the present invention exhibit low pour point equal to Compound 7 which is a conventional alkylated diphenyl ether.

TABLE 2

|  | Compound 1 Example 1 | Compound 2 Example 2 | Compound 3 Example 3 | Compound 4 Example 4 | Compound 5 Example 5 |
|---|---|---|---|---|---|
| evaporation loss rate (%) |  |  |  |  |  |
| 200° C. after 20 days viscosity ratio (times) | 16.7 | 17.1 | 11.1 | 9.6 | 6.8 |
| 200° C. | 5.4 | 5.6 | 5.4 | 5.2 | 5.0 |

TABLE 2-continued

| after 20 days acid value (mgKOH/g) | | | | | |
|---|---|---|---|---|---|
| before exam. | 0.00 | 0.01 | 0.01 | 0.01 | 0.01 |
| 200° C. after 20 days | 6.76 | 6.41 | 5.95 | 5.82 | 5.69 |

| | Compound 6 Example 6 | Compound 7 Com. Ex. 1 | Compound 8 Com. Ex. 2 | Compound 9 Com. Ex. 3 |
|---|---|---|---|---|
| evaporation loss rate (%) | | | | |
| 200° C. after 20 days | 15.6 | 21.5 | 98.2 | 32.4 |
| Viscosity ratio (times) | | | | |
| 200° C. after 20 days | 5.3 | 9.0 | impossible to measure | 11.6 |
| acid value (mgKOH/g) | | | | |
| before exam. | 0.01 | 0.01 | 0.01 | 0.01 |
| 200° C. after 20 days | 6.10 | 8.20 | impossible to measure | 8.01 |

From the results of Table 2, it is confirmed that Compounds 1 to 6 which are branched alkylated diphenyl ether of the present invention exhibit low evaporation loss rate, low viscosity ratio and low in increase of acid value compared with Compound 7 which is known as a lubricant for high temperature, and Compound 9 in which alkyl addition number is less than 2. Compound 8 which was composed almost by branched-monoalkylated diphenyl ether is high in evaporation loss and only sludge remained after heat stability test. Thus, it is impossible to measure kinematic viscosity and acid value of Compound 8.

TABLE 3

| | Compound 1 Example 1 | Compound 2 Example 2 | Compound 3 Example 3 | Compound 4 Example 4 | Compound 5 Example 5 |
|---|---|---|---|---|---|
| friction coefficient (150° C.) | 0.1625 | 0.1643 | 0.1672 | 0.1648 | 0.1669 |

| | Compound 6 Example 6 | Compound 7 Com. Ex. 1 | Compound 8 Com. Ex. 2 | Compound 9 Com. Ex. 3 |
|---|---|---|---|---|
| friction coefficient (150° C.) | 0.1660 | 0.1723 | 0.1702 | 0.1695 |

Table 3 confirms Compounds 1 to 6 which are branched alkylated diphenyl ether of the present invention exhibit low friction coefficient and are suitable for various lubricants compared with Compound 7 which is a conventional alkylated diphenyl ether.

From the above, branched alkylated diphenyl ether of the present invention exhibits fluidity at low temperature equal to a conventionally well-known and practically used alkylated diphenyl ether.

Further, the present compound is low in evaporation amount in heat stability test and is suppressed in increase of acid value compared with a conventional alkylated diphenyl ether and conventional monoalkyl addition product which are widely used as a base oil for a lubricant for high temperature and heat-resistant grease.

The base oil for a lubricant for high temperature and heat-resistant grease is most required to be suppressed in increase of acid value. Therefore, the present compound is confirmed to be excellent in heat resistance compared with a conventional alkylated diphenyl ether.

INDUSTRIAL APPLICABILITY

The present compound and composition are not only usable as a base oil for various lubricants such as bearing oil, fluid bearing oil, oil-impregnated bearing oil, oil-impregnated plastics oil, gear oil, engine oil, gas turbine oil, automatic transmission fluid, vacuum pump oil, other machine oil and hydraulic fluid, but also usable as a base oil for grease. Further, the present compound can be added to or used conjointly with other synthetic base oil, and is suitable to expand design width of lubricants. In addition, the present compound is not only usable as lubricants but also as plasticizer, refrigerating oil or the like.

The invention claimed is:

1. A compound of the formula (2)

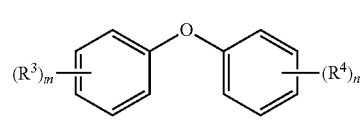

(2)

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$; and the compound of the formula (2) contains monoalkylated diphenyl ether in an amount of about 0.1 to 20 mole %.

2. A compound of the formula (2) obtained by an addition reaction of diphenyl ether and a branched α-olefin of the formula (1) or its corresponding branched alkyl halide

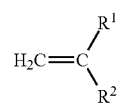

(1)

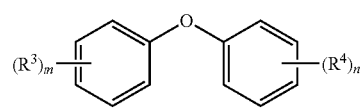

(2)

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$; and the compound of the formula (2) contains monoalkylated diphenyl ether in an amount of about 0.1 to 20 mole %.

3. A compound of the formula (2) obtained by an addition reaction of diphenyl ether derivative of the formula (3) and a branched α-olefin of the formula (1) or its corresponding branched alkyl halide

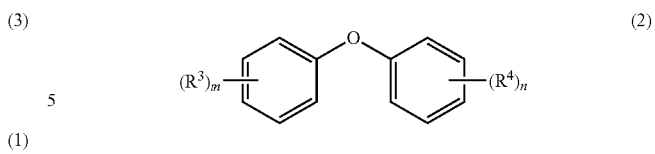
(3)

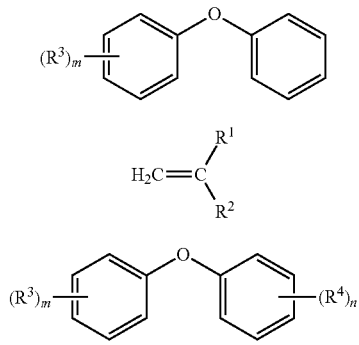
(1)

(2)

wherein $R^1$ and $R^2$ are the same or different and are a hydrocarbon group having 4 to 12 carbon atoms, $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$; and the compound of the formula (2) contains monoalkylated diphenyl ether in an amount of about 0.1 to 20 mole %.

4. A compound of the formula (2) as defined claim 1 wherein a ratio of the carbon at benzyl position being quaternary is 45 to 95 mole %.

5. A compound of the formula (2) as defined claim 1 wherein 50 to 90 mole % of the benzylic carbons of each $R^3$ and $R^4$ are quaternary.

6. A compound of the formula (2) as defined in claim 1 wherein 50 to 65 mole % of the benzylic carbons of each $R^3$ and $R^4$ are quaternary.

7. A compound of the formula (2) as defined in claim 1 wherein $R^3$ and $R^4$ are each 1-butyl-1-methylheptyl, 1-methyl-1-pentyloctyl, 1-hexyl-1-methylnonyl, 1-heptyl-1-methyldecyl, 1-methyl-1-octylundecyl or 1-decyl-1-methyltridecyl.

8. A compound of the formula (2) as defined in claim 1 wherein $2.0 \leq m+n \leq 2.94$.

9. A lubricating oil which is usable at high temperature containing a compound of the formula (2)

wherein $R^3$ and $R^4$ are the same or different and are a branched hydrocarbon group having 10 to 26 carbon atoms, 42 to 100 mole % of the benzylic carbons of each $R^3$ and $R^4$ are quaternary, m and n are each a real number of at least zero, and $2.0 \leq m+n \leq 3.0$; and the compound of the formula (2) contains monoalkylated diphenyl ether in an amount of about 0.1 to 20 mole %.

10. A compound of the formula (2) as defined in claim 2 wherein a ratio of the carbon at benzyl position being quaternary is 45 to 95 mole %.

11. A compound of the formula (2) as defined in claim 2 wherein 50 to 90 mole % of the benzylic carbons of each $R^3$ and $R^4$ are quaternary.

12. A compound of the formula (2) as defined in claim 2 wherein 50 to 65 mole % of the benzylic carbons of each $R^3$ and $R^4$ are quaternary.

13. A compound of the formula (2) as defined in claim 2 wherein $R^3$ and $R^4$ are each 1-butyl-1-methylheptyl, 1-methyl-1-pentyl octyl, 1-hexyl-1-methylnonyl, 1-heptyl-1-methyldecyl, 1-methyl-1-octylundecyl or 1-decyl-1-methyltridecyl.

14. A compound of the formula (2) as defined in claim 2 wherein $2.0 \leq m+n \leq 2.94$.

15. A compound of the formula (2) as defined in claim 3 wherein a ratio of the carbon at benzyl position being quaternary is 45 to 95 mole %.

16. A compound of the formula (2) as defined in claim 3 wherein 50 to 90 mole % of the benzylic carbons of each $R^3$ and $R^4$ are quaternary.

17. A compound of the formula (2) as defined in claim 3 wherein 50 to 65 mole % of the benzylic carbons of each $R^3$ and $R^4$ are quaternary.

18. A compound of the formula (2) as defined in claim 3 wherein $R^3$ and $R^4$ are each 1-butyl-1-methylheptyl, 1-methyl-1-pentyloctyl, 1-hexyl-1-methylnonyl, 1-heptyl-1-methyldecyl, 1-methyl-1-octylundecyl or 1-decyl-1-methyltridecyl.

19. A compound of the formula (2) as defined in claim 3 wherein $2.0 \leq m+n \leq 2.94$.

\* \* \* \* \*